US005776058A

United States Patent [19]

Levinson et al.

[11] Patent Number: 5,776,058
[45] Date of Patent: Jul. 7, 1998

[54] PRESSURE-ATTACHED PRESENTING PART FETAL PULSE OXIMETRY SENSOR

[75] Inventors: Mitchell Levinson, Pleasanton; Jessica Warring, Millbrae; Steven L. Nierlich; Phillip S. Palmer, both of San Leandro, all of Calif.

[73] Assignee: Nellcor Puritan Bennett Incorporated, Pleasanton, Calif.

[21] Appl. No.: 701,351

[22] Filed: Aug. 13, 1996

[51] Int. Cl.$^6$ ............................................. A61B 5/00
[52] U.S. Cl. ............................................. 600/338
[58] Field of Search ............................ 128/633, 634, 128/664, 665; 600/338, 339, 313, 473, 476

[56] References Cited

U.S. PATENT DOCUMENTS

| | | | |
|---|---|---|---|
| 3,402,717 | 9/1968 | Doherty | 128/351 |
| 3,825,342 | 7/1974 | Lubbers et al. | 128/634 |
| 3,827,428 | 8/1974 | Hon et al. | 128/2.06 E |
| 4,136,681 | 1/1979 | Hon | 128/2 R |
| 4,244,375 | 1/1981 | Farrar et al. | 128/642 |
| 4,281,659 | 8/1981 | Farrar et al. | 128/635 |
| 4,299,232 | 11/1981 | Zilianti | 128/642 |
| 4,537,197 | 8/1985 | Hulka | 128/633 |
| 4,543,965 | 10/1985 | Pack et al. | 128/748 |
| 4,658,825 | 4/1987 | Hochberg et al. | 128/634 |
| 5,024,226 | 6/1991 | Tan | 128/633 |
| 5,099,842 | 3/1992 | Mannheimer et al. | 128/633 |
| 5,109,849 | 5/1992 | Goodman et al. | 128/633 |
| 5,154,175 | 10/1992 | Gunther | 128/633 |
| 5,218,962 | 6/1993 | Mannheimer et al. | 128/633 |
| 5,247,932 | 9/1993 | Chung et al. | 128/633 |
| 5,361,757 | 11/1994 | Smith et al. | 128/633 |
| 5,377,675 | 1/1995 | Ruskewicz et al. | 128/634 |
| 5,411,024 | 5/1995 | Thomas et al. | 128/634 |
| 5,417,207 | 5/1995 | Young et al. | 600/476 |

FOREIGN PATENT DOCUMENTS

| | | |
|---|---|---|
| 2132539 | 9/1993 | Canada. |
| 4304693 A1 | 8/1994 | Germany. |
| WO89/09566 | 10/1989 | WIPO. |
| WO91/07910 | 6/1991 | WIPO. |
| WO91/15996 | 10/1991 | WIPO. |

Primary Examiner—Robert L. Nasser
Assistant Examiner—Eric F. Winakur
Attorney, Agent, or Firm—Townsend and Townsend and Crew

[57] ABSTRACT

A presenting part fetal pulse oximeter sensor which does not penetrate the fetus' skin, and does not rely on a vacuum for attachment is provided. The fetal sensor of the present invention is held in place by pressure applied to the fetus by a number of different mechanisms. In one embodiment, the sensor is held in place against the fetus by a rigid rod, with the pressure being applied by the physician or technician's hand on the rod. This type of a sensor is useful for spot-checking, where continuous monitoring is not needed. In another embodiment, a pre-loaded spring is coupled between the rod and the sensor head to prevent too much pressure being applied by the user.

8 Claims, 6 Drawing Sheets

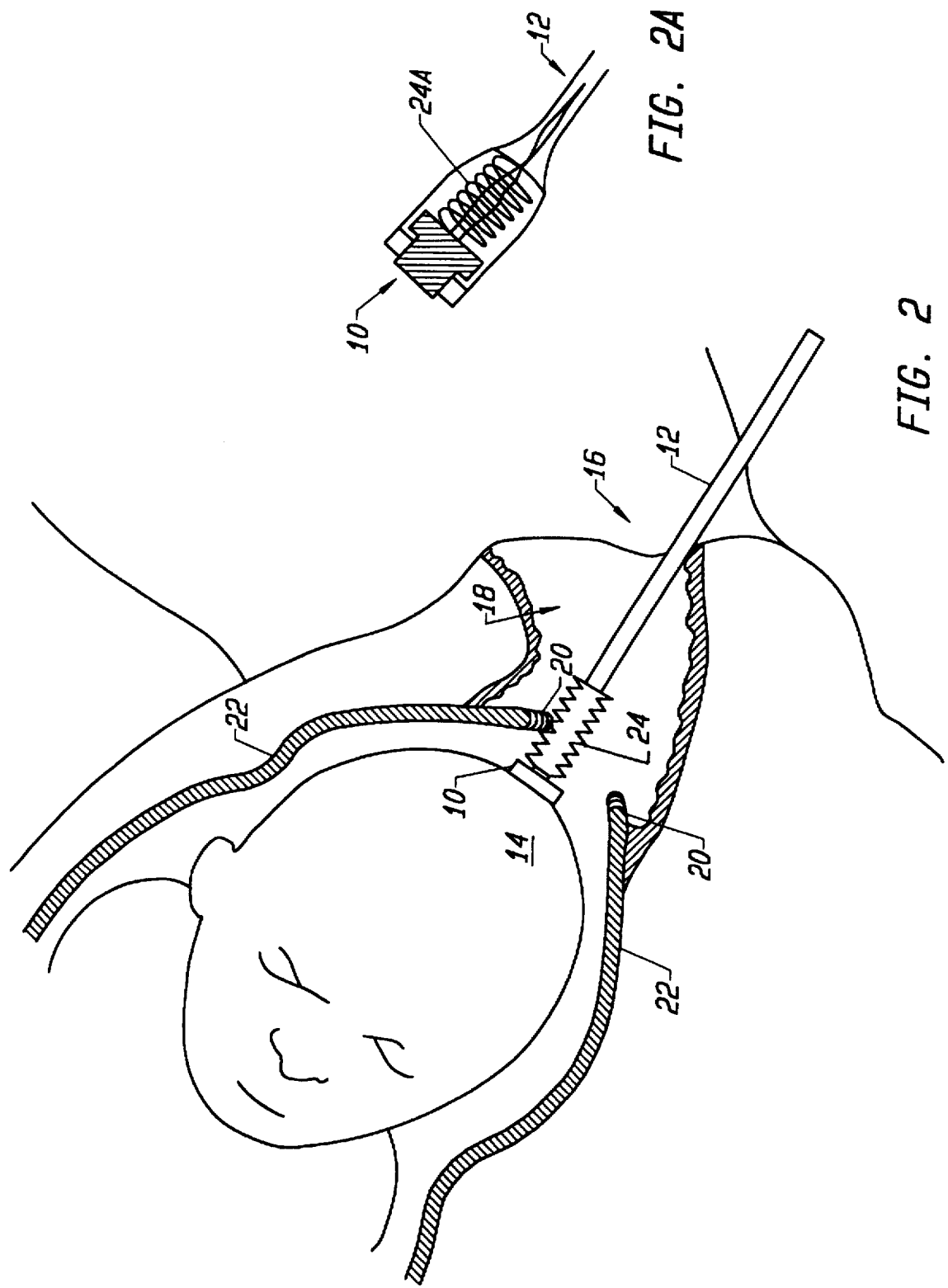

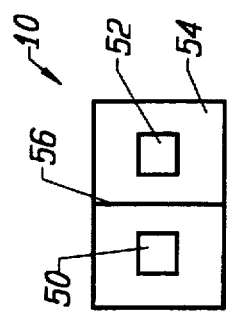
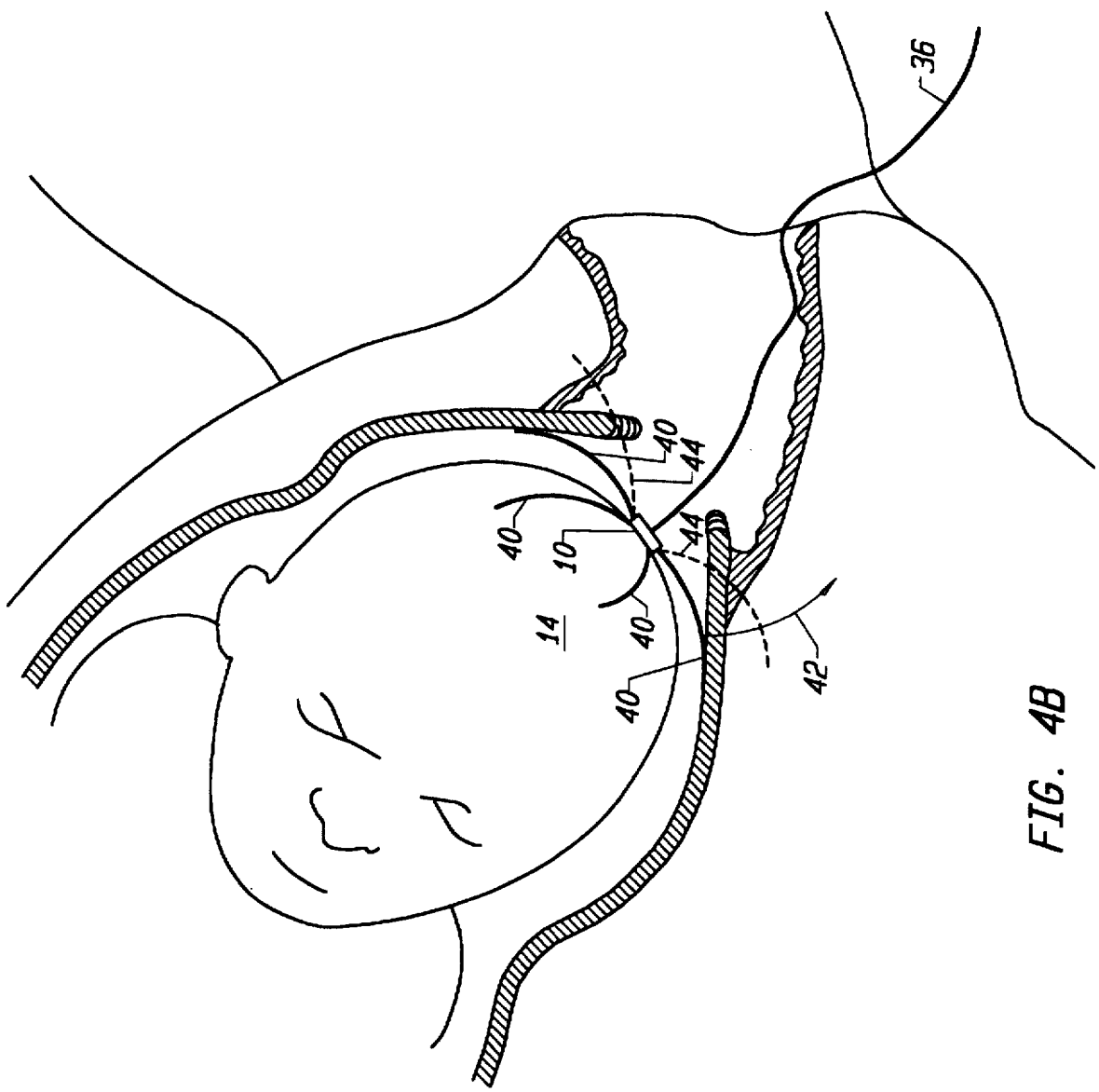

PRESSURE-ATTACHED PRESENTING PART FETAL PULSE OXIMETRY SENSOR

BACKGROUND OF THE INVENTION

The present invention relates to a non-invasive pulse oximetry fetal intrauterine sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Known non-invasive sensors include devices that are secured to a portion of the body, such as a finger, ear or the scalp. In animals and humans, the tissue of these body portions is perfused with blood and the tissue surface is readily accessible to the sensor.

It is desirable that photoelectric pulse oximetry also be useful for monitoring the blood flow characteristics and constituents of a fetus. For example, monitoring fetal oxygen levels provides an effective way to detect and provide indications for treating hypoxia in the fetus during labor. However, known sensors adapted for use on infants or adults are not suited for intrauterine placement.

The environment in which the non-invasive intrauterine sensor must operate is fluid-filled (e.g., by amniotic fluid) and is only accessible through the restricted opening of the cervix. Visual inspection of the fetus and the sensor is likewise restricted. Moreover, the operating environment presents certain variants that interfere with detection of the fetal blood flow characteristics using known pulse oximetry techniques. For example, the presence of the waxy vernix caseosa, hair, mucus, blood and dead tissue cells on top of the fetal tissue surface against which the sensor is to be positioned create a problem in establishing contact between the optical components of the sensor and the surface of blood-perfused tissue. Detection of fetal blood flow characteristics by pulse oximetry is particularly complicated by the relatively low perfusion and low oxygen saturation of blood in fetal tissue. These environmental factors prevent known sensors from providing reliable information needed to calculate fetal blood characteristics.

It is known that positive attachment of a sensor to the tissue surface improves the quality of the photoelectric signal provided by the sensor. Positive attachment to a human's tissue may be obtained by vacuum, adhesives, tapes or devices such as clothespin-type clips. However, fetal tissue is relatively moist and there is limited access to the tissue surface. Consequently, conventional adhesives or tapes or clips are not adapted for intrauterine use.

There are two basic types of fetal sensors, presenting part sensors and beyond the presenting part sensors. "Presenting part" refers to the region of the fetus that, during labor, resides external to the cervical Os. "Beyond the presenting part" falls within the uterus and extends out to the cervical Os. Sensors beyond the presenting part can typically use the uterine wall to bias the sensor against the fetus. For the presenting part, however, the fetus' scalp is typically exposed to the open birth canal, and such biasing is not as readily available, with positive attachment usually being used.

Presenting Part Sensors

Known techniques for presenting part sensors include invasive attachment to fetal tissue, such as by a screw attachment penetrating the tissue, or vacuum attachment mechanisms.

Examples of presenting part sensors include U.S. Pat. No. 3,827,428 which discloses a heartbeat sensor using a coil screw for attaching to the fetus' scalp. Pulse oximeter and other sensors which use such a spiral or screw-type arrangement are also shown in U.S. Pat. Nos. 4,281,659; 4,658,825; 5,154,175; 5,361,757; 5,411,024; and German Published Application No. DE4304691A1.

Examples of vacuum-type fetal sensors include that shown in U.S. Pat. No. 4,938,218 and PCT Published Application No. WO91/15996, which shows a bellows for providing a low-pressure vacuum source. U.S. Pat. No. 4,537,197 shows another vacuum attachment fetal sensor.

A number of other designs are also known. U.S. Pat. No. 4,299,232 shows a combination of a suction adhesion with a suction-cup type attachment, in conjunction with an electrical pole which pierces the fetus' skin. U.S. Pat. No. 5,024,226 requires a bore hole in the brain of the patient. U.S. Pat. No. 4,543,965 uses an inflatable membrane to bias the sensor against the fetus at the presenting part.

Non-Presenting Part Sensors

Other fetal sensors are designed to go beyond the presenting part. For instance, U.S. Pat. No. 5,247,932 shows a bladder between the fetus and the uterine wall which presses the active face of the sensor against the fetus' skin. U.S. Pat. No. 5,377,675 discloses a sensor using a fulcrum to bias the sensor against the fetus. PCT Published Application No. WO91/07910 uses an inflatable sac to wedge the sensor against the fetus.

The intrauterine probe sensor must be safely and reliably deliverable to the point of contact with the fetus. It is desirable that intrauterine fetal monitoring be available early in labor, for example, to detect and treat hypoxia in the fetus during labor. Contact with the fetus can be made after natural rupture of the amniotic membrane by manually inserting a probe sensor into the uterus from the vagina, but access to the fetus through the vaginal canal is restricted by the cervix, which may be only slightly dilated to one or two centimeters when the membrane ruptures. Thus there is need for a fetal probe sensor that can be delivered to the fetus through a slightly dilated cervix, and a delivery system for doing so safely and reliably.

A presenting part sensor is often desirable for a variety of reasons. First, it is less invasive than a beyond the presenting part sensor. Second, a presenting part sensor may be used for spot-checking saturation rather than continuous monitoring. Third, a presenting part sensor may be necessary for monitoring fetus' located high in the uterus. Fourth, a presenting part sensor is easy to place and may be more reliably attached than a beyond-the-presenting part sensor.

U.S. Pat. No. 5,099,842 shows a cluster of bumps over the emitter and/or detector of a pulse oximeter fetal sensor. These bumps are intended to provide a combing or scrubbing action to remove debris from the fetus' skin as the sensor is placed on the fetus so as to allow better light transmission into and out of the fetal tissue. These bumps are indicated as being over the emitter and detector, not the rest of the face of the sensor adjacent to the fetus.

SUMMARY OF THE INVENTION

The present invention provides a fetal pulse oximeter sensor which does not penetrate the fetus' skin, and does not rely on a vacuum or an adhesive for attachment. The fetal sensor of the present invention is held in place by pressure applied to the fetus by a number of different mechanisms.

In one embodiment, the sensor is held in place against the fetus by a rigid rod, with the pressure being applied by the physician or technician's hand on the rod. This type of a sensor is useful for spot-checking, where continuous monitoring is not needed. In another embodiment, a pre-loaded spring is coupled between the rod and the sensor head to prevent too much pressure being applied by the user.

In another embodiment, at least a pair of pre-loaded springs are attached to the sensor head. The springs are held adjacent the sensor during insertion, such as by inserting them through a tube. Once in place, the springs are released, allowing them to hold the sensor head against the fetus' head by biasing against the internal cervical or uterine walls. The pre-biased direction of the spring force can be either toward or away from the fetus, with the spring constructed, in each case, so that it will contact the uterine or cervical walls in either manner. In a first embodiment, the sensor tries to "climb-in" further into the uterus, biasing the sensor against the fetus. In another embodiment, the spring is braced against the uterine wall where it is not trying to climb-in, but cannot back out, keeping the sensor in contact with the fetus' head.

For a further understanding of the nature and advantages of the present invention, reference should be made to the following description taken in conjunction with the accompanying drawings.

BRIEF DESCRIPTION OF THE DRAWINGS

FIG. 2 is a second embodiment of the sensor of FIG. 1 including a compression spring;

FIG. 2A shows a coil spring embodiment of the sensor in FIG. 1, using an internal coil spring;

FIGS. 4A and 4B are diagrams of an alternate embodiment of a spring-loaded sensor biased to "climb-in"; and FIG. 5 is a diagram of a sensor head used in the embodiments of FIGS. 1–4.

DESCRIPTION OF THE PREFERRED EMBODIMENT

Figure 1:
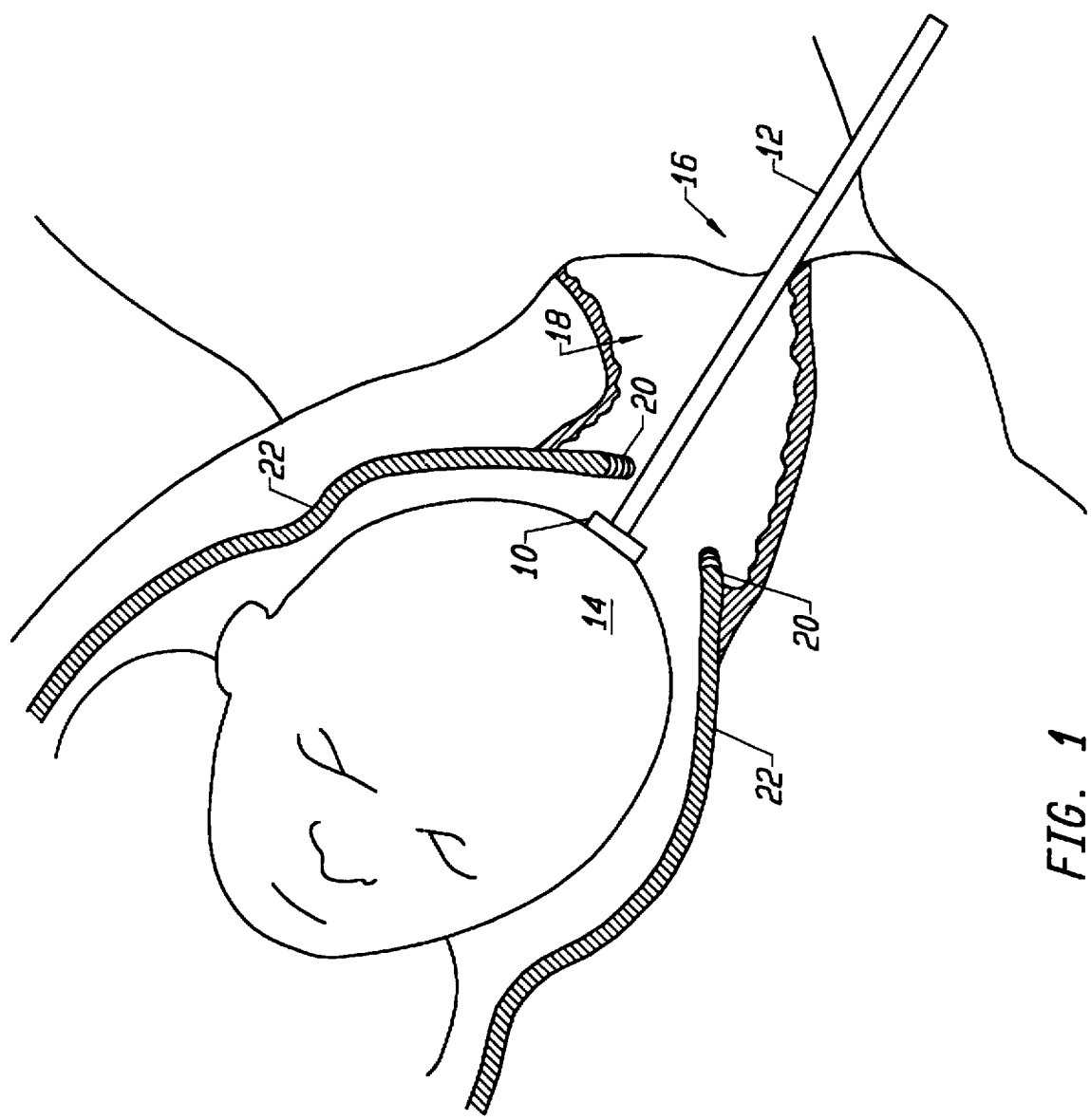
FIG. 1 is a diagram of a first embodiment of a spot-checking sensor with a rigid rod applied to a fetus' head.

FIG. 1 illustrates a sensor 10 mounted on a rigid rod (or member) 12 and applied by force of the physician or technician's hands against a fetus' head 14. The rod is simply inserted through the vagina 16, through the birth canal 18, past the cervix 20 and up against the fetus' head 14, which is positioned between the uterine walls 22. The sensor of FIG. 1 is designed for spot-checking the pulse oximeter readings, with it being expected that it would be held in place for 20 seconds or less in order to obtain a quick oxygen saturation reading.

FIG. 2 is an alternate embodiment of the sensor of FIG. 1. In FIG. 2, a compression spring 24 is mounted between rod 12 and sensor 10. In this example, the compression spring is a bellows. The spring, with appropriate spring rate and pre-load, will control the force between the sensor head and fetus' head and isolate the sensor head from motion of the rod.

Excessive pressure or force from a user's hands would have undesirable effect. For example, it can exsanguinate the tissue, keeping the blood out of the area underneath the sensor, thus preventing an accurate oxygen saturation measurement.

An additional benefit of the spring is that it can diminish motion artifact which is likely to occur if the user's hand is not completely steady or if the fetus or mother is moving.

This spring could alternately be placed in other positions in the apparatus of FIG. 2. For instance, a pair of rigid rods joined by an intermediate spring could be used, or the spring could be at a handle grasped by the physician or other user. FIG. 2A shows a coil spring embodiment of the sensor in FIG. 1, using an internal coil spring 24a.

Figure 3A:
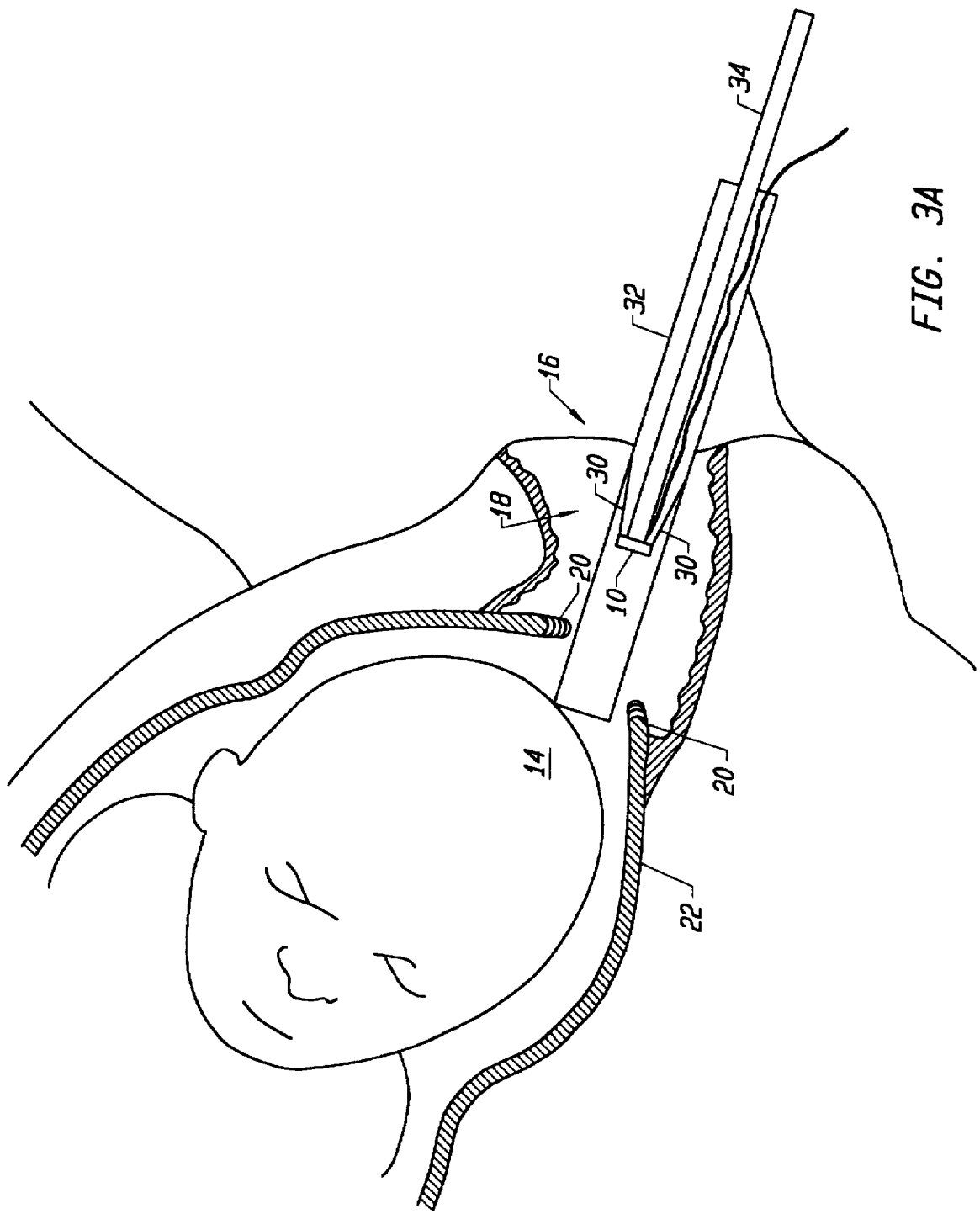
FIGS. 3A and 3B are diagrams of an embodiment of a spring-loaded sensor being inserted through a tube.
Figure 3B:
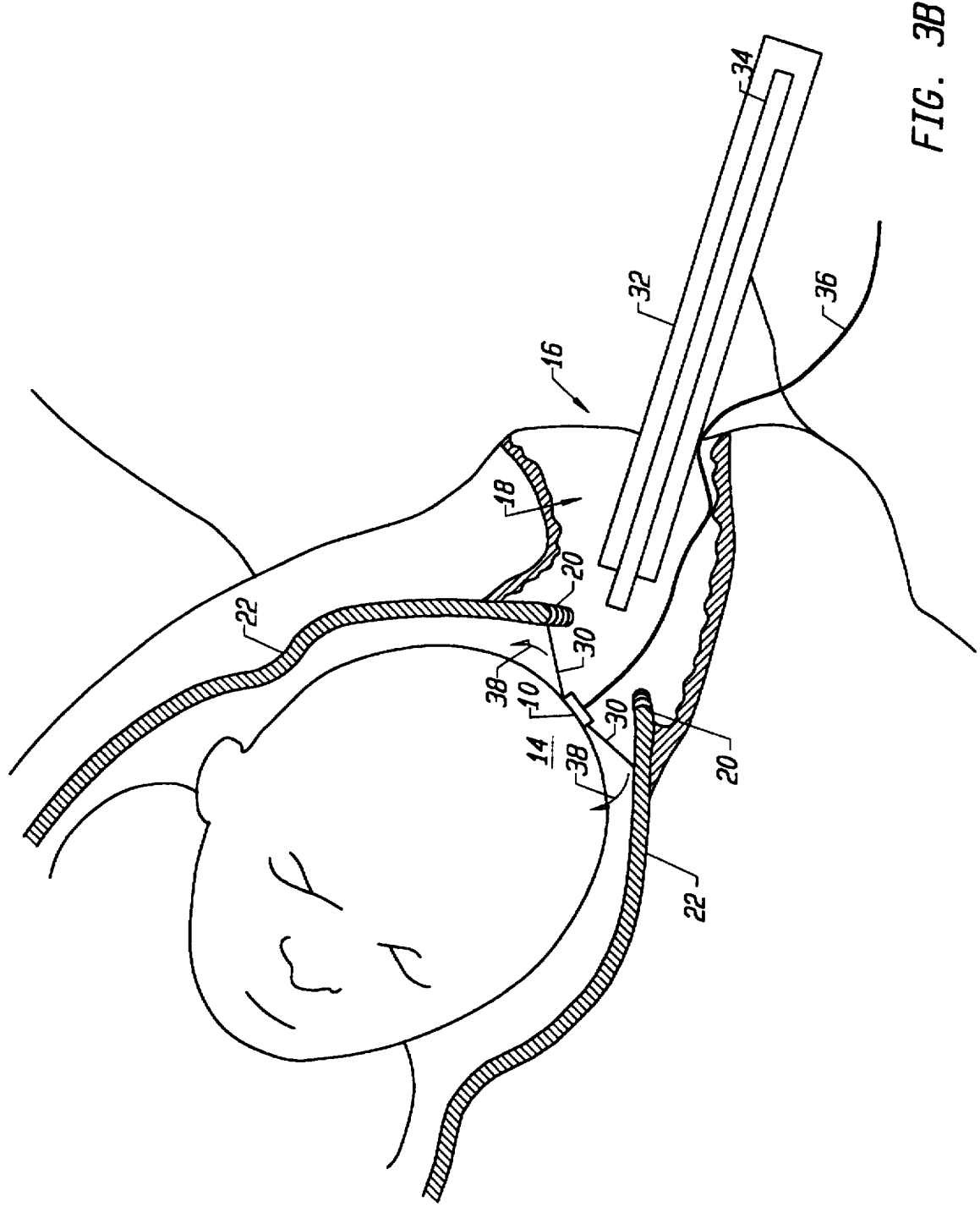

FIGS. 3A and 3B illustrate the insertion of another embodiment of the present invention. The sensor 10 of FIG. 3A has a pair of leaf springs 30 attached to it, which are biased outward to spread. In order to avoid this spreading during insertion, the sensor is inserted through a tube 32.

Once in place, as shown in FIG. 3B, the leaf springs 10 expand outward until they contact the cervical wall 20 or the uterine wall 22, or perhaps, a portion of the walls of the birth canal 18. The tube 32 and a placement tool 34 can then be removed, with only the cable 36 attached to sensor 10 extending out of the mother's body. The tube 32 can either be pulled over the far end of cable 36, or cable 36 could extend out of the insertion end of the tube, such that once sensor 10 is pushed out of the insertion end of the tube, cable 36 will be free at that point.

The force of leaf springs 30 is in a direction indicated by the arrows 38. As can be seen, this force will bias the sensor against fetus 14 as the fetus ascends into the cervical region.

Figure 4A:
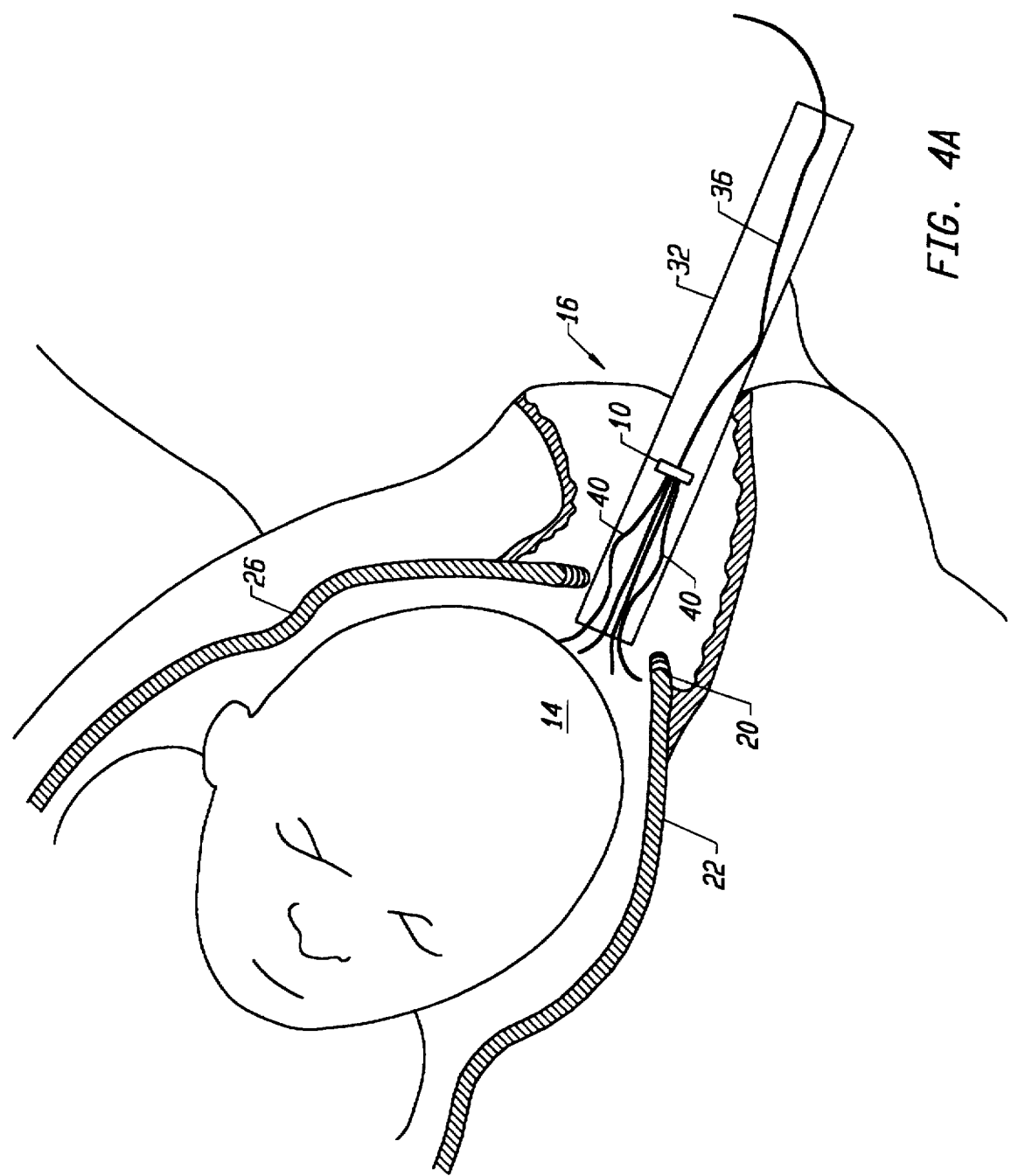

FIGS. 4A and 4B show an alternate embodiment of the present invention set forth in FIGS. 3A and 3B, in which the springs are inserted in the other direction. In FIG. 4B, a sensor head 10 has a number of springs 40 attached to it. The springs are held together upon insertion by some means, for example a tube. Upon insertion through the birth canal, the tips of the springs come into proximity to the fetal presenting part. The springs are then released, for example by withdrawing the tube, and the springs attempt to move outward and "climb-in" to the uterus as shown in FIG. 4B. The springs are biased to move in a direction indicated by arrow 42, trying to assume a pre-biased position indicated by dotted lines 44. As can be seen, the springs will thus wedge against the inside of the mother, forcing the sensor 10 against the fetus' head 14. The sensor thus tries to "climb-in" to the interior of the uterus, pushing the sensor up against the fetus' head 14. The distinction between the embodiments of FIGS. 3A and 3B and 4A and 4B is that in FIG. 3 the sensor is between the fetal head and the contact point with the uterus. In FIG. 4, the fetal head is between the contact point and the sensor (the contact point of the springs against the uterine wall is further into the uterus in FIG. 4).

The sensor of FIGS. 4A and 4B can be inserted in a manner similar to that shown in FIGS. 3A and 3B, using an insertion tube. In this embodiment, however, the springs could be pointing forward towards the fetus, not back away from it, when compressed into the tube.

FIG. 5 illustrates the face of a sensor 10 using the embodiments of FIGS. 1 to 4. The sensor includes a light emitter and a light detector 52 which are spaced from each other. The sensor can have a pliable body 54, which may, if desired, be pre-shaped to the anticipated shape of a fetus' head. Such a pliable body would naturally adapt to the shape of a fetus' head. Alternately, the sensor may be rigid, and may include an optional light barrier 56 to prevent shunting between the emitter and detector.

Multiple embodiments of sensor 10 may be utilized, as is well-known in the art. For instance, the emitter and detector may have bumps molded over them in a transparent window, such as shown in U.S. Pat. No. 5,099,842. These bumps would provide a scrubbing effect to allow the sensor to be moved and positioned up against the fetus' head, pushing its way through hair or other solids which may impede direct contact with the fetus' scalp.

As will be understood by those of skill in the art, the present invention may be embodied in other specific forms without departing from the spirit or essential characteristics thereof. For example, the springs may be held by hand rather than using an insertion tube as shown in the embodiments of FIGS. 3A and 3B. Alternately, the number of springs may be varied in the embodiments of FIGS. 3A, 3B and 4. In another embodiment, the sensor may include a light detector and emitter on its body, with electrical wires extending therefrom. Alternately, a fiber-optic cable could extend from the sensor body lo to a light emitter and detector which are external to the mother or at some position therebetween. Accordingly, the above embodiments are merely illustrative of the present invention, and reference should be made to the appended claims which set forth the scope of the invention.

What is claimed is:

1. A perinatal pulse oximeter sensor for temporary application to a fetus and providing a signal corresponding to blood oxygen saturation, comprising:

a sensor head having a fetus engaging surface for engagement with a presenting part of said fetus with applied pressure;

light emitting means connected to said sensor head for emitting light of at least two wavelengths directed in a predetermined direction at said presenting part of said fetus;

light detecting means mounted in said sensor head for collecting light from said light emitting means scattered through said fetus, and providing said signal corresponding to blood oxygen saturation; and a rigid member having a longitudinal axis connected to said sensor head with said longitudinal axis aligned with said predetermined direction having sufficient length for inserting said sensor head into a vagina and for applying said pressure to said sensor head from external to said vagina.

2. The sensor of claim 1 wherein said light emitting means and light detecting means comprise fiber optic cables.

3. The sensor of claim 1 further comprising a biasing means, coupled between said rigid member and said sensor head, for regulating the amount of force applied to said sensor head.

4. The sensor of claim 3 wherein said biasing means is a pre-loaded spring.

5. A perinatal pulse oximeter sensor for temporary application to a fetus and providing a signal corresponding to blood oxygen saturation, comprising:

a sensor head having a fetus engaging surface for engagement with a presenting part of said fetus with applied pressure;

light emitting means connected' to said sensor head for emitting light of at least two wavelengths directed at said presenting part of said fetus;

light detecting means mounted in said sensor head for collecting light from said light emitting means scattered through said fetus, and providing said signal corresponding to blood oxygen saturation; and a rigid housing having sufficient length to insert said sensor head into a vagina;

biasing means, coupled between said housing and said sensor head, for applying said pressure to said sensor head.

6. The sensor of claim 5 wherein said biasing means comprises a spring between said housing and said sensor head.

7. The sensor of claim 5 wherein said biasing means comprises a spring internal to said housing for extending said sensor head partially out of said housing.

8. The sensor of claim 7 wherein said spring is pre-loaded.

* * * * *